United States Patent [19]

Nishiyama et al.

[11] 4,216,007

[45] Aug. 5, 1980

[54] 4-[4-(5-TRIFLUOROMETHYL-2-PYRIDYLOXY)PHENOXY]-2-PENTENOIC ACID ESTERS USEFUL AS A HERBICIDE

[75] Inventors: Ryuzo Nishiyama, Takatsuki; Takahiro Haga; Nobuyuki Sakashita, both of Kusatsu, all of Japan

[73] Assignee: Ishihara Sangyo Kaisha, Ltd., Osaka, Japan

[21] Appl. No.: 34,039

[22] Filed: Apr. 27, 1979

[30] Foreign Application Priority Data

Apr. 27, 1978 [JP] Japan .................................. 53/49272

[51] Int. Cl.² ...................... A01N 9/22; C07D 213/64
[52] U.S. Cl. ...................................... 71/094; 546/302
[58] Field of Search ........................... 546/302; 71/094

[56] References Cited

U.S. PATENT DOCUMENTS

| 3,954,442 | 5/1976 | Becker et al. .......................... 71/108 |
| 4,046,553 | 9/1977 | Takahashi et al. ........................ 71/94 |
| 4,105,435 | 8/1978 | Nishiyama et al. ....................... 71/94 |
| 4,115,102 | 9/1978 | Takahashi et al. ........................ 71/94 |
| 4,152,328 | 5/1979 | Nishiyama et al. ...................... 546/302 |

*Primary Examiner*—Alan L. Rotman
*Attorney, Agent, or Firm*—Sughrue, Rothwell, Mion, Zinn and Macpeak

[57] ABSTRACT

4-[4-(5-Trifluoromethyl-2-pyridyloxy)phenoxy]-2-pentenoic acid esters, a herbicidal composition containing the same, and a method of controlling weeds using the same.

13 Claims, No Drawings

4-[4-(5-TRIFLUOROMETHYL-2-PYRIDYLOXY)-PHENOXY]-2-PENTENOIC ACID ESTERS USEFUL AS A HERBICIDE

BACKGROUND OF THE INVENTION

1. Field of the Invention

This invention relates to a novel compound useful as a herbicide for agriculture and horticulture, to a herbicidal composition containing the same, and to a method of controlling weeds using the same.

2. Description of the Prior Art

In recent years, a number of herbicides have been developed and put to practical use. These herbicides have contributed to a saving of labor and an increased production in agriculture. However, there is still room for improvements, and novel chemicals which have reduced effects on useful cultivated plants but have a strong herbicidal action on undesirable plants and which are very safe in regard to environmental pollution have been desired. For example, phenoxyalkanecarboxylic acids, of which 2,4-dichlorophenoxyacetic acid is representative, which have been known for a long time, have superior controlling effects on broad-leafed weeds and still find wide-spread use. However, since phenoxyalkanecarboxylic acids have only a slight activity on gramineous weeds which are the main noxious weeds, and are phytotoxic to broad-leafed plants which include many crops and cultivated trees, these chemicals have only a limited application.

SUMMARY OF THE INVENTION

The present invention provides 4-[4-(5-trifluoromethyl -2-pyridyloxy)phenoxy]-2-pentenoic acid esters of the formula (I):

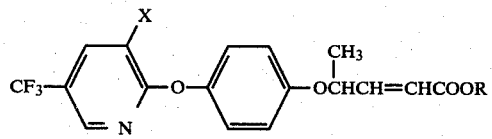

wherein X is a hydrogen atom or a halogen atom, and R is a ($C_1$–$C_4$) alkyl group.

The invention further provides a herbicidal composition comprising a herbicidally effective amount of at least one compound of the above general formula (I) and agriculturally acceptable adjuvants.

Still further, the invention provides a method for controlling weeds comprising applying a herbicidally effective amount of the above-described herbicidal composition to the weeds.

DETAILED DESCRIPTION OF THE INVENTION

The compound of the formula (I) of this invention useful as a herbicide (hereinafter, "herbicidal compound") is a novel compound, and has a unique herbicidal activity which differs from the herbicidal activities of known types of herbicidal compounds. The herbicidal compound of this invention has the following three important characteristics.

(1) The compound of the formula (I) has a strong selective herbicidal activity toward gramineous plants. On the other hand, since the compound affects broad-leafed plants to only a slight extent, especially those which have grown to some extent, it can be used with high safety on broad-leafed crops or cultivated trees. In other words, the compound of this invention has quite a reverse selectivity to and far higher selectivily than known phenoxyalkanecarboxylic acids.

(2) The compound of the formula (I) has great translocatability in the plant structure. The compound is absorbed by the foliage and roots of a plant, and mainly causes a decay of meristematic cells in the nodes, which leads to a withering, falling down and death of the plant. Accordingly, even when applied only to a very limited part of the plant structure, the compound exhibits a strong herbicidal activity, and weeds which have grown considerably are withered and killed due to the activity of the compound of this invention.

(3) The compound of the formula (I) has excellent regrowth controlling activity towards perennial gramineous weeds and safety on cotton as compared with the known 4-phenoxy- or 4-(2-pyridyloxy)phenoxyalkanecarboxylic acids. With respect to the withering and killing of perennial gramineous weeds which are difficult to control, the compound of the formula (I) has a higher translocatability than 4-phenoxy- or 4-(2-pyridyloxy)phenoxyalkanecarboxylic acids and exerts sufficient effects at the portion of the plant to which it is translocated that the plant, including the roots thereof, is withered and killed and the regrowth of the plants is controlled. Accordingly, the compound of the formula (I) is quite useful in eradication of undesirable plants with a small number of treatments.

In the above-described definition of the formula (I), suitable examples of halogen atoms which may be employed as substituent X include a chlorine atom, a bromine atom and a fluroine atom. Suitable examples of ($C_1$–$C_4$) alkly groups which can be employed as R include a methyl group, an ethyl group, an n-propyl group, an isopropyl group, an n-butyl group, an isobutyl group, a sec-butyl group and a tert-butyl group.

The herbicidal compounds of the present invention of the formula (I):

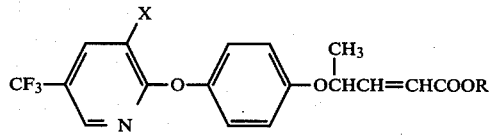

wherein X and R are as defined previously, can be produced by the methods described below.

Method A

A 2-halo-5-trifluoromethylpyridine of the formula (II):

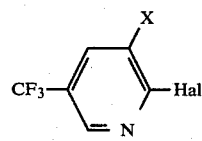

wherein X is the same as defined hereinbefore, and Hal is a halogen atom such as a chlorine atom or a bromine atom, and hydroquinone are first condensed, e.g., using equimolar amounts of the compound of the formula (II) and the hydroquinone, in the presence of an alkaline material in an amount of 1 to 1.2 molar times the amount of the hydroquinone, at a temperature of at least 50° C., preferably 70° to 180° C., preferably under an inert atmosphere, e.g., of nitrogen, for 1 to 20 hours, preferably 1 to 10 hours, to form a 4-(5-trifluoromethyl-2-pyridyloxy)phenol of the formula (III):

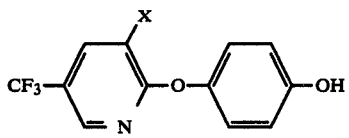
(III)

wherein X is the same as defined hereinbefore.

Then, the compound of the formula (III) and a 4-halo-2-pentenoic acid compound of the formula (IV):

(IV)

wherein Hal is a halogen atom such as a chlorine atom or a bromine atom, and R is the same as defined hereinbefore, are second condensed, e.g., using equimolar amounts of the compound of the formula (III) and the compound of the formula (IV), in the presence of an alkaline material in an amount of 1 to 1.2 molar times the amount of the compound of the formula (III), at a temperature of 40° to 200° C. at a pressure of preferably atmospheric pressure for 0.5 to 10 hours to form the object compound of the present invention of the formula (I).

Examples of suitable alkaline materials which can be used in all of the condensation reactions described above are alkali metal hydroxides such as sodium hydroxide or potassium hydroxide, and alkali metal carbonates such as sodium carbonate or potassium carbonate. A ketone such as acetone, methyl ethyl ketone or methyl isobutyl ketone, or a polar aprotic solvent such as dimethylformamide, diemthylacetamide, dimethyl sulfoxide, N-methylpyrrolidone, hexamethylphosphoramide or sulfolane, can be used in the first condensation reaction as a solvent. And a ketone such as acetone, methyl ethyl ketone or methyl isobutyl ketone, or toluene can be used in the second condensation reaction as a solvent.

Method B

The 2-halo-55-trifluoromethylpyridine of the formula (II) and a hydroquinone mono($C_1$-$C_4$) alkyl ether are first condensed, e.g., using equimolar amounts of the compound of the formula (II) and the hydroquinone mono($C_1$-$C_4$) alkyl ether, in the presence of an alkaline material in an amount of 1 to 1.2 molar times the amount of the hydroquinone mono($C_1$-$C_4$)alkyl ether, at a temperature of at least 50° C., preferably 70° to 180° C., at a pressure of preferably atmospheric pressure for 1 to 20 hours, preferably 1 to 10 hours, to form a compound of the formula (V):

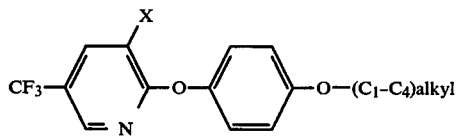
(V)

wherein X is the same as defined hereinbefore.

The ($C_1$-$C_4$)alkyl moiety of the compound of the formula (V) is dealkylated in the presence of a dealkylating agent in an amount of 1.5 to 2.0 molar times the amount of the compound of the formula (V) to form the 4-(5-trifluoromethyl-2-pyridyloxy)phenol of the formula (III).

Then, the compound of the formula (III) and the 4-halo-2pentenoic acid compound of the formula (IV) are second condensed, e.g., using equimolar amounts of the compound of the formula (III) and the compound of the formula (IV), in the presence of an alkaline material in an amount of 1 to 1.2 molar times the amount of the compound of the formula (III), at a temperature of 40° to 200° C. at a pressure of preferably atmospheric pressure for 0.5 to 10 hours to form the object compound of the present invention of the formula (I).

Examples of suitable alkaline materials and suitable solvents which can be used in the first and second condensation reactions described above are the same as those described in Method A.

When pyridine hydrochloride is used as a dealkylating agent in the dealkylation, the reaction temperature is desirably 50° to 250° C., more desirably 130° to 200° C., the pressure is preferably atmospheric pressure, and the reaction time is most generally 1 to 10 hours. When a hydrohalic acid having a concentration of 40 to 60% by weight such as hydrobromic acid or hydroiodic acid is used as a dealkylating agent, the dealkylating reaction is desirably carried out in the presence of a ($C_1$-$C_4$) fatty acid solvent, such as acetic acid or acetic anhydride, in an amount of 1 to 50 times the volume of the compound of the formula (V) for 1 to 10 hours at a pressure of preferably atmospheric pressure at a temperature of 90° to 150° C.

Method C

Hydroquinone and the 4-halo-2-pentenoic acid compound of the formula (IV) are first condensed [the hydroquinone is used in an amount of 1 to 5 molar times the amount of the compound of the formula (IV)], in the presence of an alkaline material in an amount of 1 to 1.2 molar times the amount of the compound of the formula (IV) at more than room temperature, preferably at a temperature of 50° to 180° C., at a pressure of preferably atmospheric pressure for 1 to 20 hours, preferably 1 to 10 hours, to form a p-hydroxyphenoxy-2-pentenoic acid compound of the formula (VI):

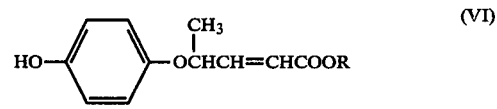
(VI)

wherein R is the same as defined hereinbefore.

Then, the compound of the formula (VI) and the 2-halo-5-trifluoromethylpyridine of the formula (II) are second condensed, e.g., using equimolar amounts of the compound of the formula (VI) and the compound of the formula (II), in the presence of an alkaline material in an amount of 1 to 1.2 molar times the amount of the compound of the formula (VI) at a temperature of at least 50° C., preferably 70° to 180° C., at a pressure of preferably atmospheric pressure for 1 to 20 hours, preferably 1 to 10 hours to form the object compound of the present invention of the formula (I).

Examples of suitable alkaline materials which can be used in the first and second condensation reactions described above are the same as those described in Method A.

Examples of suitable solvents which can be used in the first and second condensation reactions described above are the same as those described in the case of the first condensation reaction of Method A.

The starting materials described in the above methods, i.e., the 2-halo-5-trifluoromethylpyridine of the formula (II), is described in, for example, U.S. Pat. No. 4,038,396; the hydroquinone and hydroquinone mono($C_1$-$C_4$)alkly ether are described in, for example, U.S. Pat. No. 4,046,553; and the 4-halo-2-pentenoic acid compound of the formula (IV) is described in, for example, *Chemical Abstracts,* Vol. 50, 6465e (1965).

Some specific examples of preparing the herbicidal compounds of this invention are shown below.

PREPARATION EXAMPLE 1

Preparation of Ethyl 4-[4-(5-Trifluoromethyl-2-pyridyloxy)-phenoxy]-2-pentenoate 40 ml of dimethyl sulfoxide, 4.2 g of hydroquinone, 5.0 g of 2-chloro-5-trifluoromethylpyridine and 2.3 g of potassium hydroxide were reacted with stirring in a nitrogen gas stream at 150° C. for 2 hours to obtain 2.5 g of 4-(5-trifluoromethyl-2-pyridyloxy)phenol. The thus-obtained 4-(5-trifluoromethyl-2-pyridyloxy)phenol was dissolved in 20 ml of methyl ethyl ketone, and 1.7 g of anhydrous potassium carbonate was added thereto. The mixture was reacted with stirring under reflux for 1 hour, and the reaction product thusobtained was cooled to 40° C., and 2.5 g of ethyl 4-bromo-2-pentenoate was dropwise added thereto gradually. The mixture was allowed to stir for 30 minutes and then to react under reflux for 7 hours. After completion of the reaction, the reaction product was thrown into 100 ml of water, and an oily matter was extracted with methylene chloride. The extracted phase was washed with water several times, and dried over anhydrous sodium sulfate. The solvent was evaporated off to obtain a crude product which was subsequently subjected to silica gel column chromatography using toluene as an eluent to obtain 1.5 g of the object product having a refractive index, $n_D^{23}$, of 1.5145. This was found to have a boiling point of 148°–151° C./1 mm Hg with some decomposition.

PREPARATION EXAMPLE 2

Preparation of Ethyl 4-[4-(3-Chloro-5-trifluoromethyl-2-pyridyloxy)phenoxy]-2-pentenoate To 100 ml of acetone were added 11 g of hydroquinone and 5.5 g of potassium carbonate, and 4.1 g of ethyl 4-bromo-2-pentenoate was further added thereto under reflux over a period of time of 20 minutes. The mixture was allowed to react with stirring under reflux for 3 hours, and the product thus-formed was thrown into a suitable amount of water followed by extracting with methylene chloride. The extracted phase was washed with water and dried over anhydrous sodium sulfate to obtain 7.0 g of an oily matter.

7.0 g of the thus-obtained oily matter and 6.2 g of potassium carbonate were added to 120 ml of methyl ethyl ketone, and the mixture was maintained under reflux for 30 minutes. Thereafter, the reaction product was cooled to 40° C., and 19 g of 2,3-dichloro-5-trifluoromethylpyridine was dropwise added thereto over a period of time of 30 minutes. The mixture was allowed to react with stirring under reflux for 2 hours. The completion of reaction was confirmed by means of gas chromatography, and the product was thrown into a suitable amount of water followed by extracting with methylene chloride. The extracted phase was washed with water and then dried over anhydrous sodium sulfate. The solvent was evaporated off to obtain a crude product which was subsequently distilled to obtain 3.4 g of the object product. This was found to have a boiling point of 162°–165° C./1 mm Hg with some decomposition.

Typical examples of the herbicidal compounds of the present invention are given below.

Compound No. 1 Methyl 4-[4-(5-trifluoromethyl-2-pyridyloxy)phenoxy]-2-pentenoate b.p. 143°–146° C./1 mm Hg (with some decomposition)

Compound No. 2 Ethyl 4-[4-(5trifluoromethyl-2-pyridyloxy)phenoxyl]-2-pentenoate, b.p. 148°–151° C./1 mm Hg (with some decomposition)

Compound No. 3 Butyl(n) 4-[4-(5-trifluoromethyl-2-pyridyloxy)phenoxy]-2-pentenoate, b.p. 159°–162° C./0.8 mm Hg (with some decomposition)

Compound No. 4 Ethyl 4-[4-(3-chloro-5-trifluoromethyl-2-pyridyloxy)phenoxy]-2-pentenoate, b.p. 162°–165° C./1 mm Hg (with some decomposition)

The herbicidal compound of this invention can be dispersed in water to produce an aqueous dispersion. The herbicidal compound can also be formulated into various forms such as an emulsifiable concentrate, wettable powder, water-miscible solution, dust or granules by optionally incorporating conventional agriculturally acceptable adjuvants, for example, a carrier such as diatomaceous earth, calcium hydroxide, calcium carbonate, talc, white carbon, kaolin, bentonite, or Jeeklite (trade name for kaolinite, produced by Jeeklite Co.), solvents such as n-hexane, toluene, xylene, solvent naphtha, ethanol, dioxane, acetone, isophorone, methyl isobutyl ketone, dimethylformamide, dimethyl sulfoxide or water, or an anionic or nonionic surface active agent such as a sodium alkylsulfate, a sodium alkylbenzenesulfonate, sodium ligninsulfonate, a polyoxyethylene lauryl ether, a polyoxyethylene alkylaryl ether, a polyoxyethylene fatty acid ester, or a polyoxyethylene sorbitan fatty acid ester. A suitable ratio of the compound of this invention to the adjuvant(s) ranges from about 1–90:99–10 by weight, preferably 1–70:99–30 by weight.

The herbicidal composition of this invention can also be mixed or used together with suitable agricultural chemicals such as other herbicides, insecticides or fungicides, or mixed with an agricultural agent such as a fertilizer, a solid conditioner, soil or sand, at the time of formulation or application. Sometimes, such a conjoint use brings about a better effect.

Some typical examples of herbicidal formulations containing the compound of this invention are shown below.

FORMULATION EXAMPLE 1

20 parts by weight of ethyl 4-[4-(5-trifluoromethyl-2-pyridyloxy)phenoxy]-2-pentenoate, 60 parts by weight of xylene and 20 parts by weight of Sorpol 2806B (trade name for a mixture of a polyoxyethylene phenyl phenol derivative, a polyoxyethylene alkylaryl ether, a polyoxyethylene sorbitan alkylate, and an alkylaryl sulfonate, produced by Toho Chemical Co., Ltd.), as a surface active agent, were mixed uniformly to form an emulsifiable concentrate.

FORMULATION EXAMPLE 2

78 parts by weight of Jeeklite, 15 parts by weight of Carplex (trade name, principal component white carbon, produced by Shionogi Seiyaku Co., Ltd.), 2 parts by weight of Lavelin S (trade name for a sodium naphthalene sulfonateformaldehyde condensate, produced by Daiichi Kogyo Seiyaku Co., Ltd.), and 5 parts by weight of Sorpol 5039 (trade name for a sulfate of a polyoxyethylene alkylaryl ether, produced by Toho Chemical Co., Ltd.) were mixed and the mixture obtained was then mixed with ethyl 4-[4-(3-chloro-5-trifluoromethyl-2-pyridyloxy)phenoxy]-2-pentenoate in a ratio of 4:1 by weight to form a wettable powder.

FORMULATION EXAMPLE 3

58 parts by weight of bentonite, 30 parts by weight of Jeeklite and 5 parts by weight of sodium ligninsulfonate were mixed and granulated. A solution prepared by diluting 7 parts by weight of methyl 4-[4-(5-trifluoromethyl-2-pyridyloxy)phenoxy]-2-pentenoate with acetone was sprayed on the granulated components to form granules.

The unique herbicidal activity of the herbicidal compound of this invention has already been described hereinabove, but will be described in greater detail below.

(1) The compound of this invention can be used to kill gramineous weeds by pre-emergence soil treatment or foliar treatment during the growth of weeds. In particular, the compound of this invention can be used to kill gramineous weeds which have grown to a height of about 1 meter by a foliar treatment. Since the compound of this invention is extremely safe to broad-leafed agricultural crops such as soybeans, peanuts and cotton, the compound is suitable for selective weed control in upland farms.

(2) If the method of application, the dosage, and the time of application are appropriately selected, for example, if the weeds which are growing together with plants such as corn, etc., are subjected to a foliar treatment with a small amount (5–20 g/100 m$^2$), as the active ingredient, of the compound of this invention after the plant has grown to some degree, the compound of this invention can be applied to fields where gramineous crops are cultivated. Furthermore, when the dosage of the compound of this invention is excessively increased or the compound of this invention is used together with other herbicides, weeds other than gramineous weeds can be killed.

(3) The compound of this invention has low toxicity to fish, and does not affect fisheries.

The herbicidal compound of this invention is most suitably applied to upland farms, especially upland farms where broad-leafed crops are cultivated, and can also be applied to orchards, forests and various non-agricultural lands. The compound of this invention can be applied as a soil treatment or a foliar treatment in upland farm conditions or under flooded conditions. A suitable rate of application varies according to various factors such as the climate condition, the soil condition, the form of the chemical, the time of application, the method of application, or the types of cultivated crops to which it is applied and the main weeds to be controlled. When the compound of this invention is used in the form of a solid preparation (e.g., dust or granules), the amount of the active ingredient is 0.1 to 1,000 g per are (100 m$^2$), preferably 0.5 to 500 g, and more preferably 1 to 250 g, per are.

The herbicidal activity testing of the compound of this invention and the results obtained are shown below.

TEST EXAMPLE 1

Each 1/3,000 are (1/30 m$^2$) flat was charged with soil to provide an upland condition. Predetermined amounts of seeds of edible barnyard grass, radish and soybeans were sown, and covered with soil containing seeds of gramineous weeds such as large crab-grass (*Digitaria adscendens* HENR.), barnyard grass (*Echinochloa crusgalli* BEAUV.), green foxtail (*Setaria viridis* BEAUV.), etc., to a thickness of about 1 cm. Three days after sowing, a predetermined amount (100 g/are) of an aqueous dispersion of each of the herbicidal compounds shown in Table 1 below was sprayed thereon, and the growth of the weeds was visually evaluated 20 days after the spraying. The results obtained are also shown in Table 1 below. The degree of growth inhibition shown in Table 1 was evaluated on a scale of 10 grades in which 10 indicates that the growth was completely inhibited and 1 indicates no inhibition.

TABLE 1

| Compound No. | Degree of Growth Inhibition | | | |
|---|---|---|---|---|
| | Edible Barnyard Grass | Radish | Soybeans | Gramineous Weeds |
| 1 | 10 | 1 | 1 | 10 |
| 2 | 10 | 1 | 1 | 10 |
| 3 | 10 | 1 | 1 | 10 |
| 4 | 10 | 1 | 1 | 10 |

TEST EXAMPLE 2

Each 1/3,000 are (1/30 m$^2$) pot was charged with soil to provide an upland condition, and predetermined amounts of seeds of edible barnyard grass and soybeans were sown, and covered with soil to a thickness of about 1 cm. When the edible barnyard grass reached a 2.5-leaf stage, an aqueous dispersion of each of the herbicidal compounds shown in Table 2 below was applied to the foilage in a predetermined amount. Twenty days after the treatment with the compound, the growth of the barnyard grass and soybeans was visually evaluated, and the degree of growth inhibition was evaluated on the same scale as in Test Example 1. The results obtained are shown in Table 2 below.

TABLE 2

| Compound No. | Concentration of Active Ingredient | Degree of Growth Inhibition | |
|---|---|---|---|
| | | Edible Barnyard Grass | Soybeans |
| | (ppm) | | |
| 1 | 500 | 10 | 1 |
| | 200 | 10 | 1 |
| 2 | 500 | 10 | 1 |
| | 200 | 10 | 1 |
| 3 | 500 | 10 | 1 |
| | 200 | 10 | 1 |
| 4 | 500 | 10 | 1 |
| | 200 | 10 | 1 |

TEST EXAMPLE 3

Each 1/3,000 are (1/30 m²) pot was charged with soil to provide an upland condition, and predetermined amounts of seeds of barnyard grass, large crab-grass, Italian ryegrass and wild oat were sown, and covered with soil to a thickness of about 1 cm. When the grasses reached a 3–4.5 leaf stage, a predetermined amount (5g/are) of an aqueous dispersion of each of the herbicidal compounds shown in Table 3 below was foliarly applied to the respective grasses. Thirty days after the treatment with the compound, the degree of growth inhibition was visually evaluated on the same scale as in Test Example 1. The results obtained are shown in Table 3 below.

TABLE 3

| Compound No. | Barnyard Grass | Large Crab-grass | Italian Ryegrass | Wild Oat |
| --- | --- | --- | --- | --- |
| | | Degree of Growth Inhibition | | |
| 1 | 10 | 10 | 10 | 10 |
| 2 | 10 | 10 | 10 | 10 |
| 3 | 10 | 10 | 10 | 10 |
| 4 | 10 | 10 | 10 | 10 |

TEST EXAMPLE 4

Two fragments of rhizome (10–20 cm long each) of johnsongrass (*Sorghum halepence* (L.) Pers.) including 4–5 nodes were transplanted in each 1/5,000 are (1/50 m²) pot. When the johnsongrass reached a 4–5 leaf stage, a predetermined amount (10g/are) of an aqueous dispersion of each of the compounds shown in Table 4 below was sprayed thereon. Thirty days after the treatment with the compound, the degree of growth inhibition of their parts above the ground was visually evaluated on the same scale as in Test Example 1, and fifty days thereafter the number of plants regrown was evaluated. The results obtained are shown in Table 4.

TABLE 4

| Compound No. | Degree of Growth Inhibition | Number of Plants Regrown |
| --- | --- | --- |
| 1 | 10 | 0 |
| 2 | 10 | 0 |
| 3 | 10 | 0 |

While the invention has been described in detail and with reference to specific embodiments thereof, it will be apparent to one skilled in the art that various changes and modifications can be made therein without departing from the spirit and scope thereof.

What is claimed is:

1. A compound having the general formula (I):

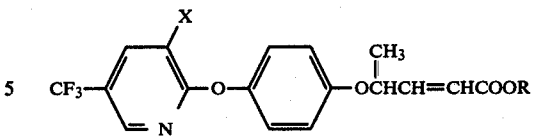

wherein X is a hydrogen atom or a halogen atom, and R is a ($C_1$–$C_4$) alkyl group.

2. The compound of claim 1, wherein X is a hydrogen atom or a chlorine atom.

3. The compound of claim 1, wherein said compound is methyl 4-[4-(5-trifluoromethyl-2-pyridyloxy)phenoxy]-2-pentenoate.

4. The compound of claim 1, wherein said compound is ethyl 4-[4-(5-trifluoromethyl-2-pyridyloxy)phenoxy]-2-pentenoate.

5. The compound of claim 1, wherein said compound is butyl(n) 4-[4-(5-trifluoromethyl-2-pyridyloxy)-phenoxy]-2-pentenoate.

6. The compound of claim 1, wherein said compound is ethyl 4-[4-(3-chloro-5-trifluoromethyl-2-pyridyloxy)-phenoxy]-2-pentenoate.

7. A herbicidal composition comprising a herbicidally effective amount of a compound having the general formula (I):

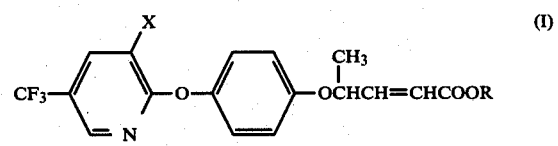

wherein X is a hydrogen atom or a halogen atom, and R is a ($C_1$–$C_4$) alkyl group, as an active ingredient, together with an agriculturally acceptable adjuvants.

8. The herbicidal composition of claim 7, wherein X is a hydrogen atom or a chlorine atom.

9. The herbicidal composition of claim 7, wherein said compound is methyl 4-[4-(5-trifluoromethyl-2-pyridyloxy)-phenoxy]-2-pentenoate.

10. The herbicidal composition of claim 7, wherein said compound is ethyl 4-[4-(5-trifluoromethyl-2-pyridyloxy)-phenoxy]-2-pentenoate.

11. The herbicidal composition of claim 7, wherein said compound is butyl(n) 4-[4-(5-trifluoromethyl-2-pyridyloxy)-phenoxy]-2-pentenoate.

12. The herbicidal composition of claim 7, wherein said compound is ethyl 4-[4-(3-chloro-5-trifluoromethyl-2-pyridyloxy)phenoxy]-2-pentenoate.

13. A method of controlling weeds comprising applying a herbicidally effective amount of the herbicidal composition of claim 7 to the weeds.

* * * * *